United States Patent
Lidor et al.

(10) Patent No.: US 6,218,566 B1
(45) Date of Patent: Apr. 17, 2001

(54) PROCESS FOR MANUFACTURING OF L-DOPA ETHYL ESTER

(75) Inventors: Ramy Lidor, Kfar Saba; Eliezer Bahar, Tel-Aviv; Anton Frenkel, Modiin, all of (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 09/437,700

(22) Filed: Nov. 10, 1999

Related U.S. Application Data

(60) Provisional application No. 60/107,820, filed on Nov. 10, 1998.

(51) Int. Cl.[7] .......................... C07C 229/00; A61K 31/24

(52) U.S. Cl. ............................................. 560/42; 514/538

(58) Field of Search ................................ 560/42; 514/538

(56) References Cited

U.S. PATENT DOCUMENTS

| | | | |
|---|---|---|---|
| 3,803,120 | 4/1974 | Felix | 260/112.5 |
| 3,939,253 | 2/1976 | Bodor et al. | 424/309 |
| 3,961,041 | 6/1976 | Nishimura et al. | 424/35 |
| 4,035,507 | 7/1977 | Bodor et al. | 424/311 |
| 4,663,349 | 5/1987 | Repta | 514/535 |
| 4,771,073 | 9/1988 | Repta | 514/535 |
| 4,826,875 | 5/1989 | Chiesi | 514/534 |
| 4,916,151 | 4/1990 | Bey et al. | 514/419 |
| 5,354,885 | 10/1994 | Milman et al. | 560/43 |
| 5,525,631 | 6/1996 | Milman et al. | 514/567 |
| 5,607,969 | 3/1997 | Milman et al. | 514/538 |

FOREIGN PATENT DOCUMENTS 1364505   8/1974   (GB) .

OTHER PUBLICATIONS

Banerjee et al., "Derivatives of 3,4–Dihydroxyphenylalanine for Peptide Synthesis" J. Org. Chem. (1976) 41(18):3056–3058 (Exhibit 12).

Bodor et al., "Improved Delivery Through Biological Membranes. 4. Prodrugs of L–DOPA" Journal of Medicinal Chemistry (1977) 20(11): 1435–1445 (Exhibit 13).

Cooper et al., "L–DOPA Methyl Ester—A Candidate for Chronic Systemic Delivery of L–DOPA in Parkinson's Disease" Clin. Neuropharmacol. (1984) 7:(1) 89–98 (Exhibit 14).

Cooper et al., "L–Dopa Esters as Potential Prodrugs: Behavioural Activity in Experimental Models of Parkinson's Disease" J. Pharm Pharmacol (Aug. 1987) 39(8): 627–635 (Exhibit 15).

El–Naggar et al., "Synthesis of Some Dipeptides Containing 2–Aminobutyric Acid, 3,4–Dihydroxyphenylalanine, Urea and Thiourea Derivatives" Polish Journal of Chemistry (1978) 52:1809–1814 (Exhibit 16).

Fix et al., "Short–Chain Alkyl Esters of L–DOPA as Prodrugs for Rectal Absorption" Pharm. Res. (1989) 6(6): 501–505 (Exhibit 17).

Juncos et al., "Levodopa Methyl Ester Treatment of Parkinson's Disease" Neurology (1987) 37 : 1242–1245 (Exhibit 18).

Lai et al., New Compounds: Synthesis of Alkyl Esters of D,L–DOPA, J. Phar. Sci. (1973) 62: 510–511 (Exhibit 19).

(List continued on next page.)

Primary Examiner—Howard C. Lee
Assistant Examiner—Leigh C. Maier
(74) Attorney, Agent, or Firm—John P. White; Cooper & Dunham LLP

(57) ABSTRACT

A process for manufacturing a highly purified, stable, non-hygroscopic, crystalline composition of L-DOPA ethyl ester. The L-DOPA ethyl ester is an active ingredient in many pharmaceutical preparations for the treatment of patients suffering from Parkinson's Disease and related indications.

28 Claims, 2 Drawing Sheets

OTHER PUBLICATIONS

Lou et al., "Direct Enantiomer Separation of Phenylalanine, DOPA and Their Intermediates by Supercritical Fluid Chromatography" Journal of Chromatography (1992) 605: 103–107 (Exhibit 20).

Marrel et al., "L–DOPA Esters as Potential Prodrugs" Eur. J. Med. Chem. (1985) 20(5): 459–465 (Exhibit 21).

Tomiuchi et al., "Enzymatic Reactions in Aqueous–Organic Media. XVII. Optical Resolution of Amino Acid Esters by Enzymatic Hydrolsis in Organic Solvents" Bull. Chem. Soc. Jpn.(1992) 65: 2599–2603 (Exhibit 22) and.

Venter et al., "Synthesis Phenylpropanolamine Derivatives as Potentitial β–Adrenergic Agents" S. Afr. Tydskr. Chem (1978) 31(4): 135–137 (Exhibit 23).

Process for Manufacture of L-DOPA Ethyl Ester

PROCESS FOR MANUFACTURING OF L-DOPA ETHYL ESTER

This application claims the benefit of U.S. Provisional Application Ser. No. 60/107,820, filed Nov. 10, 1998, the contents of which are hereby incorporated by reference into this application.

Throughout this application, various references are identified by authors and full citation. Disclosure of these publications in their entireties are hereby incorporated by reference into this application to more fully describe the state of the art to which this invention pertains.

BACKGROUND OF THE INVENTION

1. Field of the Invention

The present invention relates to a process for manufacturing a highly purified, stable, non-hygroscopic, crystalline composition of L-DOPA ethyl ester. The L-DOPA ethyl ester (also known as LDEE) is an active ingredient in many pharmaceutical preparations for the treatment of patients suffering from Parkinson's disease and related indications.

2. Description of Related Art

Typically Parkinsonian patients are routinely treated with a combination of levodopa (L-DOPA) and a DOPA decarboxylase inhibitor such as carbidopa or benserazide. Unfortunately, after an initial period of satisfactory, smooth and stable clinical benefit from L-DOPA therapy lasting on the average 2–5 years, the condition of many patients deteriorates and they develop complex dose-related as well as unpredictable response fluctuations. The causes of the response fluctuations are probably multiple and complex, but pharmacokinetic problems (primarily faulty absorption of L-DOPA) may play a critical role. There is a correlation between the clinical fluctuations and the oscillations of L-DOPA plasma levels. Many of the problems are a result of the unfavorable pharmacokinetic properties of L-DOPA, i.e., very poor solubility, poor bio-availability and short half-life in vivo.

A more suitable L-DOPA ester for therapy would be the L-DOPA ethyl ester. However, it has been difficult to develop the L-DOPA ethyl ester in a form suitable for pharmaceutical use:

"In view of the potential toxicity that might arise from methanol formation the ethyl ester would ideally have been most suitable for assessment in humans. However, the ethyl ester could not be crystallized as its hydrochloride salt because of its hygroscopic potential. The methyl ester was therefore developed for use in humans." Stocci, F. et al, Movement Disorders, 7:249–256, (1992); at 254.

L-DOPA ethyl ester is described in the literature as the hydrochloride salt. However, it is difficult to isolate as a crystalline salt and therefore was described as an amorphous solid (Fix, et al., Pharm. Research 6(6):501–505 (1989)) which is not suitable for pharmaceutical use. Cooper, et al., Clinical Neuropharmacology 7:88–89 (1984) note that L-DOPA ethyl ester hydrochloride salt is hygroscopic and difficult to crystallize during synthesis. Clearly, a pure, stable, non-hygroscopic form of L-DOPA ethyl ester is needed for pharmaceutical purposes.

Salts and esters of L-DOPA, including the L-DOPA ethyl ester, are mentioned in Patent GB 1,342,286 for the treatment of alopecia. The only disclosure regarding the nature of the L-DOPA ethyl ester is that it can be prepared from L-DOPA by conventional methods. However, as noted above, preparation of L-DOPA ethyl ester by conventional methods yields a product which is not suitable for pharmaceutical use due to its impurity, its hygroscopicity, and its lack of stability.

Great Britain Patent No. 1,364,505 and corresponding U.S. Pat. No. 3,803,120, assigned to Hoffman-La Roche, describe the synthesis of L-DOPA ethyl ester hydrochloride salt and free base. This compound is used as an intermediate in the synthesis of other compounds and is not characterized in the patent specification. In agreement with the literature (Fix, et al., Pharm. Research 6(6):501–505 (1989); and Cooper, et al., Clin. Pharmacol. 7:88–89 (1984)) we have found that the L-DOPA ethyl ester hydrochloride salt synthesized by the methods described in these patents is hygroscopic, not stable, difficult to crystallize, and, as a result, difficult to purify. This material cannot be used for pharmaceutical compositions. Likewise, the L-DOPA ethyl ester free base as prepared in these two patents is impure and not stable and thus also is not suitable for pharmaceutical compositions. At best it can be used as a synthetic intermediate for further chemical synthesis as described in the cited patents.

Two references note the synthesis of racemic ethyl ester. (Ginssburg, et al., Zh. Obshch. Khim. 39:1168–1170 (1969) and Venter, et al., S. Afr. Tydskr. Chem. 31:135–137(1978)). Neither of these references prepare crystalline L-DOPA ethyl ester in a form suitable for pharmaceutical use and certainly there is no teaching or suggestion of the preparation of crystalline L-DOPA ethyl ester in a form suitable for pharmaceutical use. Both references prepare the material as an intermediate for the synthesis of other materials of interest.

More recently, Milman et al. (U.S. Pat. No. 5,354,885) described a new process for preparing pharmaceutically acceptable, crystalline, non-hygroscopic L-DOPA ethyl ester as free base. The Milman process provides L-DOPA ethyl ester of high purity, wherein at least 97% by weight is the L-DOPA ethyl ester while L-DOPA, as an impurity, is present in less than 1% by weight of the composition.

The crystalline, non-hygroscopic L-DOPA ethyl ester composition produced according to the Milman process is highly stable and remains as at least 97% by weight L-DOPA ethyl ester after incubation for 6 months at 40° C. The availability of L-DOPA ethyl ester in such high purity made feasible the preparation of pharmaceutical compositions of L-DOPA ethyl ester, which compositions could not be successfully developed on a commercial scale until the development of the process.

The potential for increased demand of highly purified L-DOPA ethyl ester described in the U.S. Pat. No. 5,354,885, warrants research to find a simpler, more economical process for producing L-DOPA ethyl ester of high purity. While the Milman process produced a highly purified L-DOPA ethyl ester, the process is lengthy and complicated because it involves extraction steps.

The Milman process comprises reacting L-DOPA with ethanol in the presence of thionyl chloride or an acid catalyst to yield crude L-DOPA ethyl ester hydrochloride. Then volatiles are removed from the crude L-DOPA ethyl ester hydrochloride by vacuum distillation. The residue is then dissolved with water containing a suitable antioxidant and the pH is adjusted to between 6.0 and 7.0 using a suitable base to yield a solution containing L-DOPA ethyl ester free base. To obtain the free base in the solvent phase, the solution is extracted with a suitable solvent in the presence of a suitable antioxidant. The solvent phase is then concentrated at a temperature lower than 40° C. to form a precipitate. The precipitate is then recrystallized in the presence of a second suitable solvent containing a second suitable antioxidant to yield the composition of pharmaceutically acceptable, crystalline, non-hygroscopic L-DOPA ethyl ester free base.

The present invention discloses an unexpectedly simpler process for manufacturing a composition comprising pharmaceutically acceptable, crystalline, non-hygroscopic L-DOPA ethyl ester as free base in an amount which is at least 95% by weight of the composition and L-DOPA in an amount which is less than 2% by weight of the composition.

SUMMARY OF THE INVENTION

This invention provides a novel and simplified process for preparing a composition comprising pharmaceutically acceptable, crystalline, non-hygroscopic L-DOPA ethyl ester as free base in an amount which is at least 95%, and preferably 97% and more preferably 98% by weight of the composition and L-DOPA in an amount which is less than 2% and preferably less than 0.5% by weight of the composition. The process disclosed herein is significantly simpler and more economical than prior art processes while providing the L-DOPA ethyl ester of the same high or higher purity as that of the Milman process disclosed in the U.S. Pat. No. 5,354,885.

DETAILED DESCRIPTION OF THE INVENTION

Figure 1:
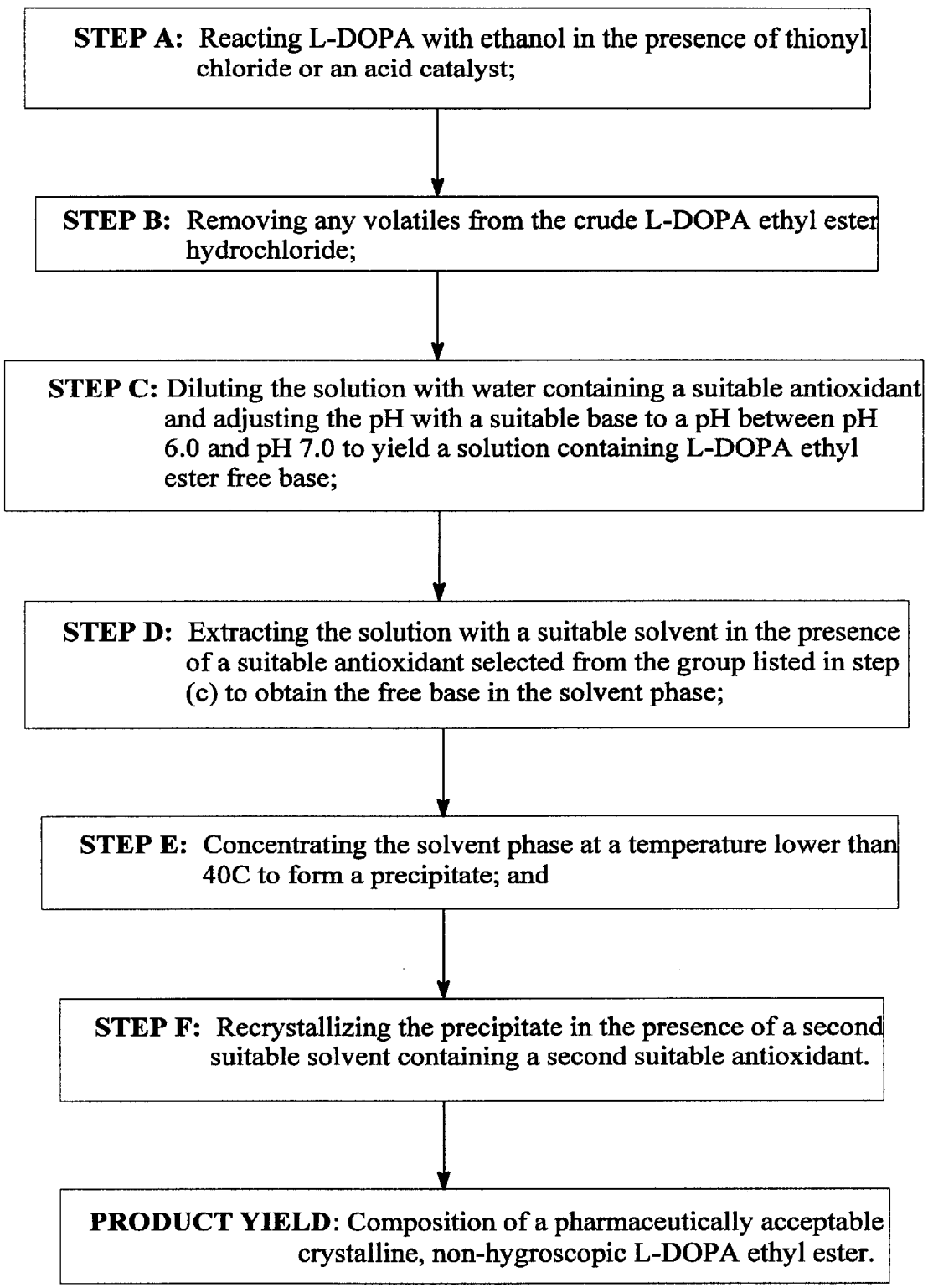
FIG. 1: A block flow diagram summarizing the Milman Process for Preparing L-DOPA Ethyl Ester as disclosed in U.S. Pat. No. 5,354,885 to Milman et al. The process comprises six (6) main steps, including an extraction procedure (step (d)).

This invention provides a process for preparing a composition comprising pharmaceutically acceptable, crystalline, non-hygroscopic L-DOPA ethyl ester as free base in an amount which is at least 95% by weight of the composition and L-DOPA in an amount which is less than 2% by weight of the composition. This process comprises the following steps (a) through (f)
(a) reacting L-DOPA with ethanol in the presence of thionyl chloride or an acid catalyst to produce a solution of crude L-DOPA ethyl ester salt;
(b) removing any residual volatiles from the solution of crude L-DOPA ethyl ester salt produced in step (a);
(c) diluting the solution from step (b) with water, and adding a cosolvent and a suitable antioxidant;
(d) adding a suitable base to the solution from step (c) under controlled conditions to precipitate a crude L-DOPA ethyl ester free base;
(e) collecting the precipitated L-DOPA ethyl ester free base from step (d);
(f) drying the precipitated crude L-DOPA ethyl ester free base collected in step (e); and
(g) recrystallizing the dried, precipitated crude L-DOPA ethyl ester free base from step (f) in the presence of a suitable solvent containing an antioxidant to produce the composition of pharmaceutically acceptable, crystalline, non-hygroscopic L-DOPA ethyl ester free base.

In one embodiment of the invention, the acid catalyst of step (a) is hydrogen chloride or toluenesulfonic acid. In the preferred embodiment of the invention, the acid catalyst of step (a) is hydrogen chloride. In one embodiment of the invention, the crude L-DOPA ethyl ester salt produced in step (a) is crude L-DOPA ethyl ester hydrochloride.

In one embodiment of the invention, the removing of residual volatiles from step (b) is effected by vacuum distillation.

In one embodiment of the invention, the residual volatiles from step (b) are ethanol and excess HCl.

In one embodiment of the invention, the cosolvent of step (c) is toluene.

In one embodiment of the invention, a suitable antioxidant of step (c) is selected from a group comprising ascorbic acid, sodium sulfite, sodium metabisulfite, propyl gallate, and vitamin E. In a specific embodiment of the invention, the antioxidant of step (c) is sodium metabisulfite.

In one embodiment of the invention, a suitable base of step (d) may be an organic or inorganic base such as sodium hydroxide or ammonium hydroxide. In a specific embodiment of the invention, a suitable base of step (d) is sodium hydroxide.

In one embodiment, the addition of a suitable base in step (d) effects an adjustment in the pH of the solution to a pH range between about 5.0 and about 9.0 to precipitate a crude L-DOPA ethyl ester free base.

In a specific embodiment, the addition of a suitable base in step (d) effects an adjustment in the pH of the solution to a pH range between 6.5–8.0 to precipitate a crude L-DOPA ethyl ester free base.

In one embodiment of the invention, the controlled conditions for step (d) are conditions in which addition of the base solution is slowly performed in a nitrogen atmosphere, and a trace amount of L-DOPA ethyl ester is added to induce formation of precipitate.

In one embodiment of the invention, the drying process in step (f) of the precipitated crude L-DOPA ethyl ester base from step (e) is effected by azeotropic distillation.

In one embodiment of the invention, a suitable solvent of step (g) is selected from a group consisting of ethyl acetate, methylene chloride, or toluene. In a specific embodiment, the suitable solvent of step (g) is ethyl acetate.

In one embodiment of the invention, an antioxidant of step (g) is selected from a group consisting of ascorbic acid, 2,6-Di-tert-butyl-4-methylphenol (BHT), butylated hydroxy anisol (BHA), propyl gallate, and vitamin E. In a specific embodiment, an antioxidant for step (f) is 2,6-Di-tert-butyl-4-methylphenol (BHT).

This invention also provides a process for preparing a composition comprising pharmaceutically acceptable, crystalline, non-hygroscopic L-DOPA ethyl ester as free base in an amount which is at least 95% by weight of the composition and L-DOPA in an amount which is less than 2% by weight of the composition, which process consists essentially of:
(a) reacting L-DOPA with ethanol in the presence of hydrogen chloride (HCl) to produce a solution of crude L-DOPA ethyl ester hydrochloride;
(b) removing ethanol and excess HCl from the solution of crude L-DOPA ethyl ester hydrochloride produced in step (a);
(c) diluting the solution from step (b) with water, toluene, and sodium metabisulfite;
(d) adding a suitable base to the solution from step (c) under controlled conditions to precipitate a crude L-DOPA ethyl ester free base;

(e) collecting the precipitated L-DOPA ethyl ester free base from step (d);
(f) drying the precipitated crude L-DOPA ethyl ester free base from collected in step (e); and
(g) recrystallizing the dried, precipitated crude L-DOPA ethyl ester free base from step (f) in the presence of a suitable solvent containing an antioxidant to produce the composition of pharmaceutically acceptable, crystalline, non-hygroscopic L-DOPA ethyl ester free base.

In one embodiment of the process, the amount of hydrogen chloride gas of step (a) is between 1–3 equivalents.

In another embodiment of the process, the amount of hydrogen chloride gas of step (a) is between 1.75–2 equivalents.

In one embodiment of the process, the base solution in step (c) is sodium hydroxide (NaOH) solution or ammonium hydroxide ($NH_4OH$).

In another embodiment of the process, the base solution in step (c) is sodium hydroxide (NaOH) solution.

In another embodiment of the process, the controlled conditions from step (d) are conditions in which addition of the sodium hydroxide solution is slowly performed in a nitrogen atmosphere, at a reaction temperature between 10–30° C. and a trace amount of L-DOPA ethyl ester is added to induce formation of precipitate.

In a further embodiment of the process, the controlled conditions from step (d) are conditions in which addition of the sodium hydroxide solution is slowly performed in a nitrogen atmosphere, at a reaction temperature between 25–30° C. and a trace amount of L-DOPA ethyl ester is added to induce formation of precipitate.

In a specific embodiment, the addition of a suitable base in step (d) effects an adjustment in the pH of the solution to a pH range between 6.5–8.0 to precipitate a crude L-DOPA ethyl ester free base. In another specific embodiment, the addition of a suitable base in step (d) effects an adjustment in the pH of the solution to a pH range between 7.6 and 7.8 to precipitate a crude L-DOPA ethyl ester base.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Description of the Process

A process for preparing a composition comprising pharmaceutically acceptable, crystalline, non-hygroscopic L-DOPA ethyl ester as free base in an amount which is at least 95%, and preferably 97% and more preferably 98% by weight of the composition and L-DOPA in an amount which is less than 2% by weight of the composition, which process comprises detailed steps A–H:

A. Reacting L-DOPA with ethanol in the presence of 1.75–2 equivalents HCl gas. The amount of HCl gas is not catalytic since one equivalent reacts with the amino group of L-DOPA.
B. Removing the volatiles (ethanol and excess HCl) from the crude L-DOPA ethyl ester hydrochloride.
C. Diluting the solution with water, adjusting the pH to 2–3 most preferably with 5N NaOH solution (at this pH range L-DOPA ethyl ester is stable in the solution and will not decompose back to L-DOPA during the distillation of the reaction mixture). 13% $NH_4OH$ solution can also be used for the precipitation of L-DOPA ethyl ester base.
D. Adding toluene as a cosolvent (prevents the sticking of the L-DOPA ethyl ester crude at the walls of the reactor during the precipitation), adjusting pH to 4–5, adding a suitable antioxidant such as sodium metabisulfite and purging out the air from the reactor by using a continuous stream of nitrogen gas.
E. Adjusting the reaction temperature to 10–30° C. (most preferably to 25–30° C.) correcting the pH to 6.5–6.7 and seeding with L-DOPA ethyl ester to induce crystallization.
F. Precipitating L-DOPA ethyl ester base by controlled (slow) addition of the base solution until pH 7.4–8.0 (most preferably 7.6–7.8) and collecting the precipitate at 5° C.
G. Drying the water from the wet precipitate by azeotropic distillation with toluene. If wet L-DOPA ethyl ester is dried in a stainless steel vacuum oven, decomposition of the material results.
H. Recrystallizing the dried precipitate in the presence of ethyl acetate containing BHT as antioxidant.

Synthesis of Crude L-DOPA Ethyl Ester

Absolute ethanol (395 g, 500 ml, 8.58 moles, 17 eq.) and L-DOPA (100 g, 0.507 moles, 1 eq.) are introduced into 1 L reactor. The batch is cooled to 15° C. and HCl(g) (37.01 g, 1.014 mole, 2 eq.) is bubbled into the reaction mixture at 15–30° C. The reaction is heated to reflux (79° C.) and kept at reflux for 3 hours. The batch is then cooled to 40° C. and 350–400 ml of solvent is distilled out under vacuum during 1.5–2 hours (50 mbar, jacket temperature 60° C.). Deionized water (220 ml) is introduced, the pH of the solution is adjusted to 2–3 with 5N NaOH solution (65 ml) and 170 ml of the reaction mixture is distilled out during 1.5-2 hours (50 mbar, jacket temperature 50° C.). Toluene (20 ml) is added to the resulting solution, the pH of the solution is adjusted to pH 4–5 with 5N NaOH solution and sodium metabisulfite (2 g, 2% w/w) is added. The operations from this stage on are done at nitrogen atmosphere. The temperature of the reaction is adjusted to 25–30° C., the pH is adjusted to 6.5–6.7 with 5N NaOH and the solution is seeded with L-DOPA ethyl ester (1 g). The precipitation is continued by controlled addition of 5N NaOH solution (70 ml/hr.) until pH 7.6–7.8, the reaction mixture cooled to 5° C. and kept at this temperature for one hour. The precipitate is collected by filtration and washed with (2×40 ml) cold water. The crude wet precipitate is dried by azeotropic distillation of the water with toluene (500 ml) under vacuum (50 mbar, jacket temperature 25–45° C.) until no more water is distilled out. The mixture is cooled to ambient temperature, L-DOPA ethyl ester (crude) is collected by filtration, washed with toluene and dried in a vacuum oven at 30–35° C. until constant weight. The yield of crude material is 85%.

Synthesis of Crystalline L-DOPA Ethyl Ester

Into 500ml reactor are introduced L-DOPA ethyl ester crude (30 g) and ethyl acetate which contains 0.01% BHT (150 ml, 5 volumes relative to L-DOPA ethyl ester weight). The batch is heated to 50° C. during half an hour and kept at this temperature until a slight turbidity remained in the solution. The hot solution is filtered through a 0.2μ filter and returned into the reactor (the time elapsed from the beginning of the crystallization until the end of filtration should not exceed 2.5 hours). The clear solution is cooled to 30° C. during 30 min. (seeded at 45° C. with L-DOPA ethyl ester, at 37–38° C. massive crystallization is observed) then cooled to 5° C. during 1 hour and kept at this temperature for another 1 hour. L-DOPA ethyl ester (cryst.) is collected by filtration, washed with 15 ml ethyl acetate which contains 0.01% BHT under nitrogen and dried in a vacuum oven at 30–35° C. until constant weight. The crystallization yield is 85%. The overall yield is 72%.

Purity of L-DOPA Ethyl Ester

The active ingredient resulting from the synthesis procedure comprises (1) L-DOPA ethyl ester in an amount which is at least 95% by weight of active ingredient; and (2) L-DOPA in an amount which is less than 2% by weight of the active ingredient.

To increase the purity of the product, additional water may be added. For example, performing the final crystallization in ethyl acetate with 1% water will result in increased purity. The amount of water to be added is easily determinable by one skilled in the art. However, it is preferable to use only ethyl acetate since the addition of water will nearly always result in loss of yield.

Levodopa ethyl ester precipitated from water has surprisingly higher purity than levodopa ethyl ester isolated via the extractive process (as performed in Milman et al.). The LDEE precipitation in water takes place at low temperatures which prevents impurities such as levodopa-levodopa ethyl ester and cyclic L-DOPA from evolving. Crystallization performed at higher temperatures (50° C.) tends to have a higher content of impurities. Therefore, the Milman process which requires extractive procedures at higher temperatures has a lower purity than the present invention.

Moreover, crude levodopa ethyl ester produced after precipitation in the subject invention may in fact have higher purity than the levodopa ethyl ester produced after crystallization for the reasons stated above. The treatment with hot (50° C.) ethyl acetate may induce increased production of impurities. However, the crystallization process is necessary for (1) controlling the particle size distribution (PSD) and (2) filtering each drug substance through a micron filter system during crystallization.

Physical Properties and Stability

L-DOPA ethyl ester as free base obtained by this process is stable, non-hygroscopic, crystalline and has a particle size in the range of: 18–180$\mu$, with an average of less than 60$\mu$.

The Novelties and Advantages of the Process

Figure 2:
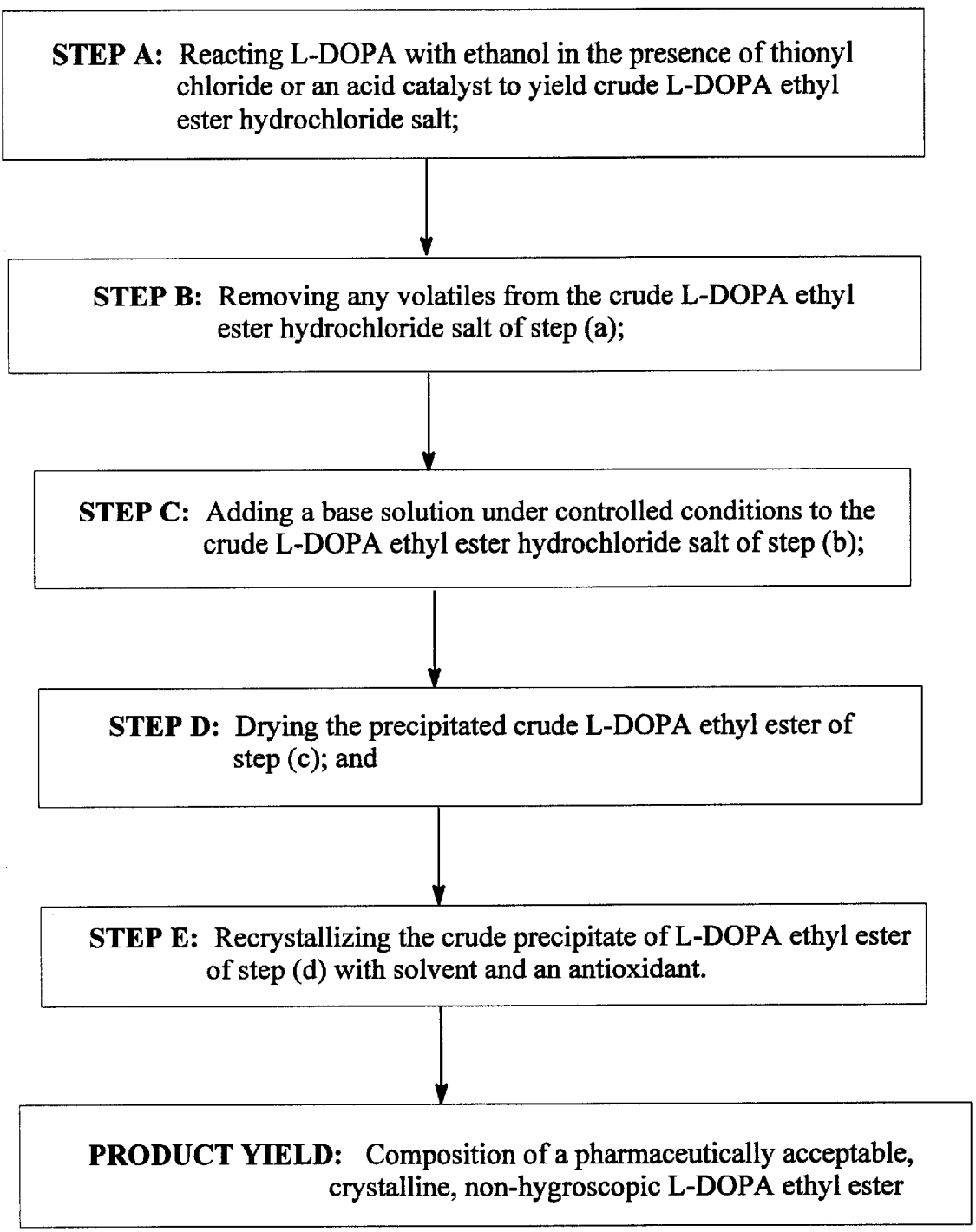
FIG. 2: A block flow diagram summarizing the Process for Manufacture of L-DOPA Ethyl Ester according to the subject invention. The process according to the subject invention is distinguished from the Milman process of FIG. 1 because it achieves the same or higher purity of L-DOPA ethyl ester suitable for pharmaceutical use in less steps.

The main advantage of the process herein is the reduced number of steps which increases efficiency and economy. Comparison between the Milman process and the presently disclosed process shows a significant difference in productivity. The Milman process and the process for the subject invention have been summarized in FIGS. 1 and 2 respectively.

The Milman process comprises reacting L-DOPA with ethanol in the presence of thionyl chloride or an acid catalyst to yield crude L-DOPA ethyl ester hydrochloride. Any volatiles are then removed by vacuum distillation, the residue is then dissolved with water containing a suitable antioxidant and the pH is then adjusted to between 6.0 and 7.0 using a suitable base to yield a solution containing L-DOPA ethyl ester free base. To obtain the free base in the solvent phase, the solution is extracted with a suitable solvent such as ethyl acetate, in the presence of a suitable antioxidant. The solvent phase is then concentrated at a temperature lower than 40° C. to form a precipitate. Recrystallization of the precipitate occurs in the presence of a second suitable solvent containing a second suitable antioxidant to yield the composition of pharmaceutically acceptable, crystalline, non-hygroscopic L-DOPA ethyl ester free base.

The Milman process (FIG. 1) requires three extractions and addition of salt to the water phase at the second extraction. The addition of salt leaves the ethyl acetate saturated with salted water which necessitates two additional washings. In addition to the complications of extractions and washings, the resulting ethyl acetate contains about 7% water. Drying this ethyl acetate/L-DOPA ethyl ester solution is an involved step in the Milman process. Because most drying agents interact with L-DOPA ethyl ester, azeotropic distillation is the best route. Since azeotropic mixture of water and ethyl acetate contains a small amount of water, and since L-DOPA ethyl ester base is very sensitive to heat (producing two impurities, cyclic levodopa and levodopa-levodopa ethyl ester), vacuum distillation is required. Vacuum distillation is time consuming and the prior art process, as a whole, wastes solvent. These complications are detrimental to the resulting yield of the product. In fact, the Milman process results in only 50% yield, even though the reflux of L-DOPA with ethanol/HCl produces 96% L-DOPA ethyl ester hydrochloride in the reaction mixture. The remaining material is in the water phase and decomposed to L-DOPA and other byproducts during the laborious work-up.

By contrast in the process of this invention (FIG. 2), after removal of volatiles, the next step is simply to adjust the pH of the solution, add toluene and sodium metabisulfite, and then a solution of sodium hydroxide in a controlled manner (temp., stirring speed, pH, rate of addition) to precipitate L-DOPA ethyl ester free base from the aqueous phase. The L-DOPA ethyl ester is then dried by azeotropic distillation with toluene and crystallized from ethyl acetate containing BHT as antioxidant. The azeotropic distillation step disclosed in this invention eliminates the need to use ethyl acetate for isolation of the final product. Elimination of the distillation step results in significant savings in solvents, their recovery, as well as time. L-DOPA ethyl ester is not easily extracted since it is also soluble to a certain extent in water.

Compared to the Milman process, the presently disclosed process is simpler and shorter because the capacity of production in the same reactors in terms of volume of output and yield is tripled. In the Milman process, the extraction step extracts the product into the organic phase (ethyl acetate) in a two system mixture (aqueous/organic), while in the presently disclosed process, the product is precipitated from an aqueous phase since there is no organic phase. The fact that the subject invention has a crystallization step starting from a dry crude levodopa ethyl ester is a great advantage since reproducibility can be achieved, while in the Milman process, crystallization was unpredictable.

Moreover, according to the present process, the precipitation of L-DOPA ethyl ester is in water at an ambient temperature so that very pure compound is obtained in greater yield than previously in prior art.

What is claimed:

1. A process for preparing a composition comprising pharmaceutically acceptable, crystalline, non-hygroscopic L-DOPA ethyl ester as free base, which process comprises:

(a) reacting L-DOPA with ethanol in the presence of thionyl chloride or an acid catalyst to produce a solution of crude L-DOPA ethyl ester salt;

(b) removing any residual volatiles from the solution of crude L-DOPA ethyl ester salt produced in step (a);

(c) diluting the solution from step (b) with water and adding a cosolvent and a suitable antioxidant;

(d) adding a suitable base to the solution from step (c) under controlled conditions to precipitate a crude L-DOPA ethyl ester free base;

(e) collecting the precipitated L-DOPA ethyl ester free base from step (d);

(f) drying the precipitated crude L-DOPA ethyl ester free base collected in step (e); and (g) recrystallizing the dried, precipitated crude L-DOPA ethyl ester free base from step (f) in the presence of a suitable solvent containing an antioxidant to produce the composition of pharmaceutically acceptable, crystalline, non-hygroscopic L-DOPA ethyl ester free base.

2. The process of claim 1, wherein the acid catalyst of step (a) is hydrogen chloride or toluenesulfonic acid.

3. The process of claim 2, wherein the acid catalyst of step (a) is hydrogen chloride.

4. The process of claim 1, wherein the crude L-DOPA ethyl ester salt produced in step (a) is L-DOPA ethyl ester hydrochloride.

5. The process of claim 1, wherein the removing of residual volatiles in step (b) is effected by vacuum distillation.

6. The process of claim 5, wherein the residual volatiles removed in step (b) are ethanol and excess HCl.

7. The process of claim 1, wherein the cosolvent of step (c) is toluene.

8. The process of claim 1, wherein the suitable antioxidant of step (c) is selected from a group consisting of ascorbic acid, sodium sulfite, sodium metabisulfite, propyl gallate, and vitamin E.

9. The process of claim 8, wherein the suitable antioxidant of step (c) is sodium metabisulfite.

10. The process of claim 1, wherein the suitable base of step (d) is sodium hydroxide or ammonium hydroxide.

11. The process of claim 10, wherein the suitable base of step (d) is sodium hydroxide.

12. The process of claim 1, wherein the addition of a suitable base in step (d) effects an adjustment in the pH of the solution to a pH range between about 5.0 and about 9.0 to precipitate a crude L-DOPA ethyl ester base.

13. The process of claim 12, wherein the addition of a suitable base in step (d) effects an adjustment in the pH of the solution to a pH range between 6.5 and 8.0 to precipitate a crude L-DOPA ethyl ester base.

14. The process of claim 1, wherein the controlled conditions from step (d) are conditions in which addition of the base solution is slowly performed in a nitrogen atmosphere, and a trace amount of L-DOPA ethyl ester is added to induce formation of precipitate.

15. The process of claim 1, wherein the drying of step (e) is effected by azeotropic distillation.

16. The process of claim 1, wherein the suitable solvent of step (f) is selected from a group consisting of ethyl acetate, methylene chloride, and toluene.

17. The process of claim 16, wherein the suitable solvent of step (f) is ethyl acetate.

18. The process of claim 1, wherein the antioxidant of step (f) is selected from a group consisting of ascorbic acid, 2,6-Di-tert-butyl-4-methylphenol (BHT), butylated hydroxy anisol (BHA), propyl gallate, and vitamin E.

19. The process of claim 17, wherein the antioxidant of step (f) is 2,6-Di-tert-butyl-4-methylphenol (BHT).

20. A process for preparing a composition comprising pharmaceutically acceptable, crystalline, non-hygroscopic L-DOPA ethyl ester as free base, which process comprises:
   (a) reacting L-DOPA with ethanol in the presence of hydrogen chloride (HCl) to produce a solution of crude L-DOPA ethyl ester hydrochloride;
   (b) removing ethanol and excess HCl from the solution of crude L-DOPA ethyl ester hydrochloride produced in step (a);
   (c) diluting the solution from step (b) with water, toluene, and sodium metabisulfite;
   (d) adding a suitable base to the solution from step (c) under controlled conditions to precipitate a crude L-DOPA ethyl ester free base;
   (e) collecting the precipitated L-DOPA ethyl ester free base from step (d);
   (f) drying the precipitated crude L-DOPA ethyl ester free base collected in step (e) ; and
   (g) recrystallizing the dried, precipitated crude L-DOPA ethyl ester free base from step (f) in the presence of a suitable solvent containing an antioxidant to produce the composition of pharmaceutically acceptable, crystalline, non-hygroscopic L-DOPA ethyl ester free base.

21. The process of claim 20, wherein the amount of hydrogen chloride gas of step (a) is between 1–3 equivalents.

22. The process of claim 21, wherein the hydrogen chloride gas of step (a) is between 1.75–2 equivalents.

23. The process of claim 20, wherein the base solution in step (c) is sodium hydroxide solution or ammonium hydroxide.

24. The process of claim 23, wherein the base solution in step (c) is sodium hydroxide solution.

25. The process of claim 20, wherein the controlled conditions from step (d) are conditions in which addition of the sodium hydroxide solution is slowly performed in a nitrogen atmosphere, at a reaction temperature between 10–30° C. and a trace amount of L-DOPA ethyl ester is added to induce formation of precipitate.

26. The process of claim 25, wherein reaction temperature is between 25–30° C.

27. The process of claim 20, wherein the addition of a suitable base in step (d) effects an adjustment in the pH of the solution to a pH range between 6.5 and 8.0 to precipitate a crude L-DOPA ethyl ester base.

28. The process of claim 27, wherein the addition of a suitable base in step (d) effects an adjustment in the pH of the solution to a pH range between 7.6 and 7.8 to precipitate a crude L-DOPA ethyl ester base.

* * * * *